United States Patent

Haag et al.

[11] Patent Number: 5,874,645
[45] Date of Patent: Feb. 23, 1999

[54] PROCESS FOR THE PREPARATION AND PURIFICATION OF 4,4'-DIHYDROXY-ALPHA-SUBSTITUTED STILBENE

[75] Inventors: Anthony P. Haag, Freeport, Tex.; Thomas A. Chamberlin, Midland, Mich.; Robert E. Hefner, Jr.; David A. Carr, both of Lake Jackson, Tex.

[73] Assignee: The Dow Chemical Company, Midland, Mich.

[21] Appl. No.: 845,747

[22] Filed: Apr. 25, 1997

[51] Int. Cl.$^6$ .................................... C07C 39/12
[52] U.S. Cl. ........................ 568/729; 568/717; 568/727
[58] Field of Search .................... 568/729, 727, 568/717

[56] References Cited

U.S. PATENT DOCUMENTS

| | | |
|---|---|---|
| 3,326,986 | 6/1967 | Dungan et al. . |
| 4,927,973 | 5/1990 | Dong et al. . |
| 5,182,340 | 1/1993 | Hefner, Jr. et al. . |
| 5,248,360 | 9/1993 | Jones, Jr. et al. . |
| 5,264,502 | 11/1993 | Hefner, Jr. et al. . |
| 5,296,570 | 3/1994 | Earls et al. . |
| 5,350,594 | 9/1994 | Unruh . |
| 5,475,155 | 12/1995 | Hefner, Jr. et al. . |

FOREIGN PATENT DOCUMENTS 905994 9/1962 Germany .

OTHER PUBLICATIONS

Zaheer et al., "Reactions of α–Halogeno–ketones with Aromatic Compounds. Part I. Reactions of Chloroacetone and 3–Chlorobutanone with Phenol and its Ethers," Journal of Chemical Society, pp. 3360–3362 (1954).

*Primary Examiner*—Michael L. Shippen

[57] ABSTRACT

A process which includes the step of heating a compound of Formula (I):

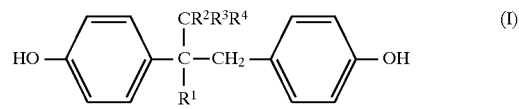

wherein $R^1$ is a hydroxyphenyl group or a group of Formula (II):

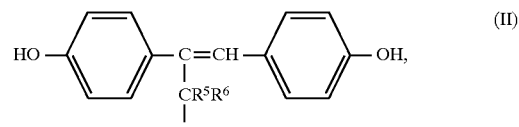

and $R^2$, $R^3$, $R^4$, $R^5$ and $R^6$ are independently in each occurrence H or a $C_{1-10}$ alkyl group; to a temperature in the range of from 100° C. to 400° C. under reaction conditions sufficient to form one or more 4,4'-dihydroxy-alpha-substituted stilbenes.

18 Claims, No Drawings

PROCESS FOR THE PREPARATION AND PURIFICATION OF 4,4'-DIHYDROXY-ALPHA-SUBSTITUTED STILBENE

BACKGROUND OF THE INVENTION

The invention relates to a process for preparing or purifying 4,4'-dihydroxy-alpha-substituted stilbenes.

The 4,4'-dihydroxy-alpha-substituted stilbenes prepared by the processes of the invention are useful in the preparation of liquid crystalline polycarbonates, polyestercarbonates, phenoxy thermoplastics, epoxy resins, polyarylates and polyesters. High purity 4,4'-dihydroxy-alpha-substituted stilbene can impart high performance properties in polycarbonates, polyestercarbonates, phenoxy thermoplastics, polyarylates and polyesters.

The reaction of alpha-haloketones with aromatic compounds, such as chloroacetone and 3-chlorobutanone with phenol and its ethers to yield 4,4'-dihydroxy-alpha-substituted stilbenes is known, see for example, *J. Chem. Soc.*, pp. 3360–2 (1954). Typically, 4,4'-dihydroxy-alpha-methylstilbene is prepared via the condensation of chloroacetone and phenol in the presence of an acid. This process also yields substantial amounts of dimeric coproducts and other impurities; see, for example, U.S. Pat. No. 5,475,155. 4,4'-Dihydroxy-alpha-substituted stilbenes prepared by these processes are useful in thermoset polymer applications which do not require high purity. The impurities resulting from these processes make the 4,4'-dihydroxy-alpha-substituted stilbenes unacceptable for use in the production of thermoplastic polymers, such as polycarbonates, polyestercarbonates, phenoxy resins, polyarylates and polyesters. Also, the relatively substantial amounts of impurities produced by the process leads to a costlier process.

What is needed is a process for preparing or purifying 4,4'-dihydroxy-alpha-substituted stilbenes that can be performed efficiently with less cost and difficulty than current preparation or purification processes. What is also needed is a process that leads to a higher purity product than can be prepared under the current processes.

SUMMARY OF THE INVENTION

In one aspect, this invention is a process comprising heating a compound of Formula (I):

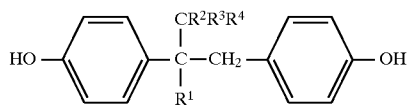

wherein $R^1$ is a hydroxyphenyl group or a group of Formula (II):

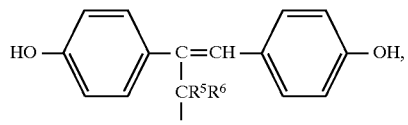

and $R^2$, $R^3$, $R^4$, $R^5$, and $R^6$ are independently in each occurrence H or a $C_{1-10}$ alkyl group; to a temperature in the range of from 100° C. to 400° C. under reaction conditions sufficient to form one or more 4,4'-dihydroxy-alpha-substituted stilbenes.

The process of the invention allows the efficient preparation and/or purification of 4,4'-dihydroxy-alpha-substituted stilbenes with less cost than the current preparation and purification processes. Processes involving the reaction of phenols and alpha-haloketones to prepare 4,4'-dihydroxy-alpha-substituted stilbenes (hereafter, collectively, "DHAS" compounds) typically result in some formation of the compounds of Formula (I). These compounds are difficult to remove completely from DHAS compounds using conventional techniques such as recrystallization and distillation. Relatively pure forms of DHAS compounds are particularly desirable for use in thermoplastic polymer applications, since the compounds of Formula (I) are tri-functional and tetra-functional, and may significantly affect the processibility of polymers prepared therefrom, due to the formation of crosslinked polymer species. This invention permits the purification of DHAS-containing compositions which also contain compounds of Formula (I) by a process which results in a relatively high overall yield to the desired DHAS compound in a relatively cost-effective manner. These and other advantages of the invention will be apparent from the description which follows.

DETAILED DESCRIPTION OF THE INVENTION

In Formula (I), the aryl rings may also contain other substituents, such as additional hydroxy, alkyl, alkoxy, or halogen (such as chlorine and bromine) groups, that do not interfere with the reaction as described herein. Preferably, $R^1$ is, in each occurrence, hydroxyphenyl or a group of Formula (II) wherein $R^5$ and $R^6$ are hydrogen. Preferably, $R^2$ is H or a $C_{1-4}$ alkyl group and $R^3$, $R^4$, $R^5$, and $R^6$ are H. Most preferably, $R^2$, $R^3$, $R^4$, $R^5$ and $R^6$ are H.

Compounds corresponding to Formula (I) may be obtained by any suitable method. Examples of such processes are described in Lippman, *On the Condensation of Chloroacetone with Phenols*, Ber. 45, pp. 2489–91 (1912) and in U.S. Pat. No. 4,415,723. Such compounds are also often formed as by-products of reactions between halogenated ketones and phenolic compounds wherein the reaction product of principal interest is a different compound, such as a DHAS compound. An example of such a method is described in Hefner, Jr. et al., U.S. Pat. No. 5,475,155, which describes 1,2,2-tris(hydroxyphenyl)propane and dimeric species of 4,4-dihydroxy-alpha-methylstilbene as by-products.

Accordingly, the starting materials for the processes described herein may, for example, be in the form of (i) the pure compound of Formula (I); (ii) a solution of the compound (I) in a crude reaction product of either a process to make the compound (I) or a similar compound, such as a DHAS compound, which product also may contain unreacted starting materials, solvent, DHAS compounds, and other by-products of the process, (iii) a precipitate or crystallized product obtained from such a crude reaction product, which may also contain substantial amounts of DHAS compounds and other by products, and (iv) the mother liquor remaining after precipitation or crystallization, or the residue remaining after distillation, of a portion of the compounds from the crude reaction product, containing compounds (I) in solution. If the process conditions require the starting material to be in the form of a composition containing at least 50 weight percent of the compounds of Formula I (which type of process is described below), such requirement would preclude the use of the above forms which contain major amounts of solvents or water, without further treatment to remove such. If desired, distillation techniques may be used to remove undesirable amounts of water or solvent in the starting material, particularly for processes which will not involve the use of an acid or base catalyst.

The DHAS compound obtainable by the process utilizing the compound of Formula (I) will necessarily depend on the formula of the particular compound (I). Preferred DHAS compounds correspond to Formula (III):

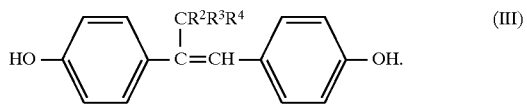

Other compounds which may be produced as a by-product of the process described herein include those of Formula (IV):

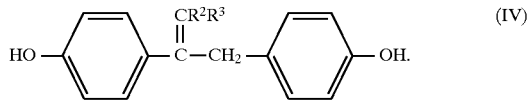

Preferably, $R^2$ is H or $C_{1-10}$ alkyl, and $R^3$ and $R^4$ are H. $R^2$ is most preferably H. Most preferably, the compound obtained by the process of the invention is trans- or cis-4,4'-dihydroxy-alpha-methylstilbene, 2,3-bis(4-hydroxyphenyl)propene or a mixture thereof.

In one preferred embodiment, the process of the invention is carried out in a reaction medium comprising at least 50 percent by weight of the compounds of Formula (I) and, optionally, compounds of Formulas (III) and (IV), and other compounds containing hydroxyphenyl groups (excluding phenol). The remainder of the reaction mixture may be comprised of compounds of Formulas (I), (III), and (IV), solvents (including phenol), or other compounds or polymers which do not significantly interfere with the formation of compounds (I) and (IV). In this embodiment, it is believed, without intending to be bound thereby, that the hydroxyphenyl groups of the compounds present in the reaction mixture provide a sufficiently acidic medium to allow the conversion to DHAS compounds to proceed, so long as the reaction medium does not contain more than a minor amount of solvents or other compounds (less than 50 percent by weight). In such embodiment, the process is preferably carried out with the compound of Formula (I) and any compounds of Formulas (III) and (IV) present therewith, in the molten state. The compounds containing hydroxyphenyl groups preferably comprise at least 75 percent by weight of the reaction mixture, and most preferably at least 90 weight percent. In such embodiment, the reaction mixture is preferably heated to a temperature of at least about 150° C., more preferably at least 180° C., most preferably at least 200° C.; but is preferably no greater than 400° C., more preferably no greater than 300° C., most preferably no greater than 250° C.

In a second preferred embodiment, the process of the invention is carried out in a reaction medium comprising: (a) at least one compound of Formula (I), and (b) at least 0.01 percent by weight, based on the weight of the compounds of Formula (I), of either an acid having a pKa of no greater than 5, or a base whose conjugate acid has a pKa of at least 5. The catalyst may be either a homogeneous or heterogeneous catalyst; if a homogeneous catalyst is used, a good dispersion of the catalyst should be obtained in the compound of Formula (I). If a heterogeneous catalyst is used, which is typically in a fixed bed, the mixing is provided by flow through of the compound of Formula (I). Examples of such preferred heterogeneous catalysts include fluoroalkylsulfonic acid or sulfonic acids bound to polymers, zeolites such as the acid form of ZSM-S, silica-alumina-water catalysts and the like.

Useful acid catalysts are those having a pKa of no greater than 5. The acid catalyst is preferably a strong protonic acid or a Lewis acid which is an electron-pair acceptor. Even more preferred acid catalysts include sulfuric acid, methanesulfonic acid, toluenesulfonic acid, a strong cation-exchange resin in sulfonic acid form, hydrogen bromide, hydrogen chloride, phosphoric acid, boron trifluoride, boron trifluoride etherate, ferric chloride or any combination thereof. A most preferred catalyst is toluenesulfonic acid.

Useful base catalysts are those whose conjugate acid has a pKa of greater than 5. Preferred base catalysts include alkali metal alkoxides, alkali metal hydroxides, alkali metal arylates, alkali metal carbonates, alkali metal acetates, and tertiary amines. Even more preferred base catalysts include sodium methoxide, sodium hydroxide, sodium phenate, sodium carbonate, potassium carbonate, potassium phenate, potassium hydroxide, triethylamine, and trioctylamine. Most preferred base catalysts include sodium hydroxide, potassium hydroxide, sodium phenate and potassium phenate.

The amount of catalyst which facilitates the formation of DHAS compounds depends upon the amount of compound of Formula (I) in the mixture, the temperature, the solvent used, if any, the catalyst used and the time of reaction desired. The amount of catalyst used is the amount which results in a high yield of the desired product. The amount of catalyst used is preferably about 0.01 percent by weight based on the weight of the compound of Formula (I) or greater, more preferably about 0.1 weight percent or greater and even more preferably about 0.5 weight percent or greater; but is preferably present in an amount of no greater than 10 weight percent, more preferably no greater than 5 weight percent, and most preferably no greater than 1 weight percent. The time of addition of the catalyst should be such that a good dispersion of the catalyst should be obtained in the compound of Formula (I), unless a supported catalyst is used which is typically in a fixed bed. If water is present in the reaction mixture, it is preferably present in an amount, based on the ratio of moles of water:moles of acid or base, of less than 10:1, more preferably less than 1:1; and most preferably less than 0.1:1.

Any solvent employed in the processes of the invention is preferably polar, substantially inert to the compound of Formula (I), the DHAS compounds, and any catalysts present, has a high boiling point and is capable of dissolving the compound of Formula (I). The boiling point of the solvent is preferably above the temperature at which the reaction occurs while being below that at which the DHAS compound will degrade, so that it can be distilled from the product without degradation. Preferably, the boiling point of the solvent is about 150° C. or greater, more preferably about 190° C. or greater and even more preferably about 200° C. or greater. Preferably, the boiling point of the solvent is less than 200° C. at 1 mm Hg. Preferred solvents include aromatic hydrocarbons, aliphatic hydrocarbons, alkyl ethers of polyalkylene glycols, sulfones, sulfoxides, ketones, ethers, amides, and phenol. More preferred solvents include alkyl ethers of polyethylene glycols, N-methylpyrrolidone, tetramethylene sulfone and diphenyl oxide. Even more preferred solvents include triethylene glycol dimethyl ether and tetramethylene sulfone. Most preferred solvents include tetramethylene sulfone. The use of phenol as a solvent may be preferred in some instances since it is normally present in the initial reaction mixture used to prepare the compounds of Formula (I), but may be less preferred in others (particularly in the presence of an acid or base catalyst) since it may react with the DHAS compounds which are present in or forming in the reaction mixture, thereby forming tris(hydroxyphenyl) compounds and reducing the amount of DHAS compounds which might be obtained using a different solvent. The contacting of the starting compounds with the solvent may be performed at ambient temperature or the temperature at which the starting compounds are being processed. If an acid or base catalyst is employed, the solvent is preferably used in an amount, based on weight ratio of solvent: the compound of Formula (I) of at least 0.1:1, more preferably at least 0.5:1; but is preferably no greater than 1000: 1, more preferably no greater than 100:1.

The processes of the invention described herein all involve heating the reaction mixture. The time required to complete the reaction depends upon the addition time of the optional catalyst, the reaction temperature, solvent presence, the heat transfer ability of the reactor employed and other such variables. The higher the temperature of the reaction, the shorter period of time that is required for the reaction to be completed, whereas lower temperatures require longer periods of time for the reaction to take place. However, if too high a temperature is used, the reaction may yield undesirable compounds. Ideally, the reaction is run for as short a period of time, at as low a temperature, and with as small of an amount of catalyst as possible, while still obtaining the desired product. The reaction can be performed as a batch process or continuous process. The reaction may be carried out at any pressure which will allow the reaction to proceed, but the preferred reaction pressure will likely depend on the volatility of the reaction solvent, if one is employed, and the desirability of removal of any of the solvents or products by distillation as the reaction proceeds. The temperature at which the reaction is conducted is the temperature sufficient to allow the formation of DHAS compounds, but below that at which significant amounts of impurities form. Preferably, the temperature at which the reaction is conducted is about 100° C. or greater, more preferably about 120° C. or greater and most preferably about 190° C. or greater. The temperature at which the reaction is conducted is preferably about 400° C. or less, more preferably about 300° C. or less and most preferably about 250° C. or less. Optionally, agitation may be used in the reactor vessel. At higher temperatures it may be preferable to carry out the process in an inert atmosphere, such as nitrogen, to avoid the oxidation of reactants or products.

Once the reaction has been completed and, optionally, the reaction mixture is cooled, the DHAS compounds may be recovered from the reaction mixture by any suitable method. Examples of such include precipitation with non-solvent and suction filtration of precipitated product, vacuum drying, distillation or solvent crystallization or combinations thereof. If the process to form the DHAS compounds is carried out in the absence of a low-boiling solvent, the DHAS compounds may be distilled from the reaction as they form. This provides the advantage of reduced exposure of the DHAS compound to temperatures which may destroy the product as it forms.

The processes of the invention are particularly desirable for use in the purification of precipitates or crystals which are mainly comprised of DHAS compounds, but which also contain significant amounts of compounds of Formula (I), such as may be obtained as a precipitate from a reaction mixture used to prepare DHAS compounds. In such purification processes, the molar ratio of the compounds of Formula (I) to other compounds containing phenolic groups, such as the compounds of Formulas (III) and (IV) may be less than 1:9 in the initial reaction mixture. Purification of such solids to the desired DHAS compounds by the use of the methods described herein may result in a higher overall yield to the DHAS compounds, since a significant amount of such compounds may be lost if other purification methods are employed, such as multiple recrystallizations.

The processes of this invention yield DHAS compounds suitable for use in thermoplastic polymer applications as well as thermoset polymer applications such as polycarbonates, polyestercarbonates, phenoxy thermoplastics, polyarylates, epoxy resins and polyesters for uses such as composites, coatings, adhesives, encapsulants, molded parts, films, filament wound products, pultruded products, castings and the like.

ILLUSTRATIVE EMBODIMENTS OF THE INVENTION

The following examples are provided to illustrate the invention, but are not intended to limit the scope thereof. All parts and percentages are by weight unless otherwise indicated.

EXAMPLE 1

A compound according to Formula (I) wherein $R^1$ is 2,3-bis(4-hydroxyphenyl)-2-propenyl and $R^2$, $R^3$, and $R^4$ are H; hereinafter, "dimer") (20.4 g containing about 5 weight percent 4,4'-dihydroxy-alpha-methylstilbene) is mixed with triethylene glycol dimethyl ether (105 mL). Toluenesulfonic acid monohydrate (0.02 g) was added to the mixture. The mixture is then heated at 1 90° C. for 4 hours. An additional 0.02 g of toluenesulfonic acid monohydrate is added and the heating continued for 9 hours. More toluenesulfonic acid monohydrate is added (0.05 g) and heating continued for 8 hours. The solution is cooled to room temperature, diluted with 400 mL of water, cooled to 15° C. and the resulting solid collected by suction filtration. The solid is vacuum dried at 60° C. for 15 hours and then at 80° C. for 22 hours. The resulting solid weighs 20.6 g and contains 72 weight percent trans-4,4'-dihydroxy-alpha-methylstilbene (hereinafter "trans-DHAMS") as determined by external standard high performance liquid chromatographic (HPLC) analysis.

EXAMPLE 2

A mixture of dimer and dihydroxy-alpha-methylstilbene (20.7 g with about 50 weight percent dimer) is dissolved in triethylene glycol dimethyl ether (106 g) by stirring at room temperature. Toluenesulfonic acid monohydrate (0.007 g) is added and the solution is heated at 190° C. for 3 hours. At that time, another 0.002 g of toluenesulfonic acid monohydrate is added and heating continued another 2.5 hours. The reaction mixture is diluted with 400 mL of water, stirred at 4° C. for 0.5 hour and the solids collected by suction filtration. After air drying for three days and then heating at 70° C. in an air oven for 13 hours, 22.0 g are obtained. External standard HPLC analysis confirms the product contains 84 weight percent trans-DHAMS.

EXAMPLE 3

A compound according to Formula (I) wherein $R^1$ is 4-hydroxyphenyl and $R^2$, $R^3$, and $R^4$ are H; hereinafter, "Tris") (10.0 g) and sodium hydroxide (0.2 g) are heated in 50 mL of tetramethylene sulfone at 220° C. under a nitrogen atmosphere for 3 hours. After cooling to 65° C., a short path distillation head is attached and 38 mL of distillate are collected (pot temp. <130° C., head temperature of 100° C.

to 110° C.). The still bottoms are diluted with 190 mL of 1 percent aqueous HCl. The resulting mixture is suction filtered and yields a sticky solid which is heated at 80° C. with water (100 mL) overnight. The resulting solid is collected by suction filtration and weighs 4.1 g after drying. External standard HPLC analysis shows that this product contains 84 weight percent trans-DHAMS, or 3.44 g (49 percent yield).

EXAMPLE 4

Tris (10.0 g) and sodium phenoxide trihydrate are heated in a Kugelrohr distillation apparatus at 0.05 to 0.10 mm Hg at 200° C. As distillate is collected, the temperature on the inside of the Kugelrohr is increased from 200° C. to 220° C. over 1 hour. Distillate weighs 6.2 g and contains 17 area percent phenol, 18 percent Tris, 36 percent DHAMS, 6 percent 2,3-bis(4-hydroxyphenyl)propene (hereinafter, "exo-DHAMS") and 23 percent cis-DHAMS. The still bottoms contain 84 percent unconverted Tris and 6 percent DHAMS. Based on HPLC area percent analysis of distillate, the yield of trans-DHAMS and isomers is 4.03 g (56 percent yield, based on the amount of converted Tris).

EXAMPLE 5

DHAMS is prepared via the condensation of phenol:chloroacetone:concentrated sulfuric acid using 15:1:1 molar stoichiometry at −10° C. HPLC analysis reveals the following area percent composition in the relative order of elution for the crystalline product:

| Compound | Area Percent |
| --- | --- |
| trans-DHAMS | 95.3 |
| exo-DHAMS | Not Detected |
| dimer I | 1.8 |
| cis-DHAMS | 1.6 |
| dimer II | 1.3 | wherein dimer I and II are trans- and cis-isomers, respectively, of Formula (I) wherein $R^1$ is 2,3-bis(hydroxyphenyl)-2-propenyl and $R^2$, $R^3$, and $R^4$ are H.

A portion (30 mg) of the crystalline product obtained above is heated in an aluminum pan under a nitrogen atmosphere flowing at 35 cubic centimeters per minute at a heating rate of 10° C. and then holds at 225° C. for the next 30 minutes, followed by rapid cooling to 25° C. The resulting product is analyzed by HPLC to provide the following results:

| Compound | Area Percent |
| --- | --- |
| trans-DHAMS | 72.8 |
| exo-DHAMS | 7.0 |
| dimer I | Not Detected |
| cis-DHAMS | 20.2 |
| dihydroxy-alpha-methylstilbene isomer | trace |
| dimer II | Not Detected |

The results of the HPLC analysis reveal a collective 100.0 area percent DHAMS isomers with no detectable dimers remaining.

What is claimed is:

1. A process comprising heating a reaction mixture comprising at least: (a) one or more compounds of Formula (I):

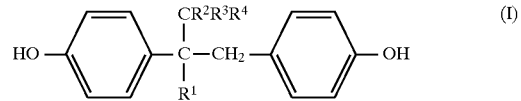

wherein $R^1$ is a hydroxyphenyl group or a group of Formula (II):

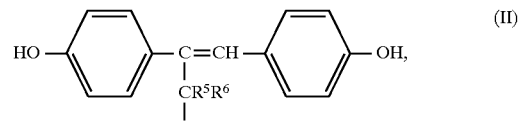

and $R^2$, $R^3$, $R^4$, $R^5$ and $R^6$ are independently in each occurrence H or a $C_{1-10}$ alkyl group; and, (b) at least 0.01 percent by weight, based on the weight of component (a), of an acid having a pKa of no greater than 5; wherein said mixture contains less than 10 moles of water per mole of acid; to a temperature in the range of from 100° C. to 400° C. under reaction conditions sufficient to convert at least a portion of the compounds of Formula (I) to compounds of Formula (III):

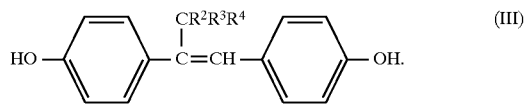

and $R^2$, $R^3$ and $R^4$ are H.

2. The process of claim 1 wherein $R^1$ is hydroxyphenyl or

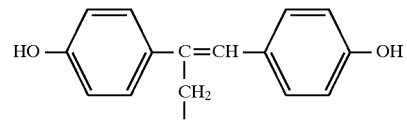

3. The process of claim 1 wherein the acid is methanesulfonic acid, toluenesulfonic acid, a cation-exchange resin in the sulfonic acid form, sulfuric acid, boron trifluoride, boron trifluoride etherate, hydrogen chloride, hydrogen bromide, phosphoric acid, ferric chloride, or a mixture thereof.

4. The process of claim 1 wherein the acid is toluenesulfonic acid.

5. The process of claim 1 wherein the amount of acid is present in an amount of less than 10 percent by weight, based on the weight of the compound of Formula (I).

6. The process of claim 1 wherein the reaction mixture contains a solution of compound (I) and the solvent is selected from the group consisting of aromatic hydrocarbons, aliphatic hydrocarbons, alkyl ethers of polyalkylene glycol, sulfones, sulfoxides, ketones, ethers, phenols, amides, or mixtures thereof.

7. The process of claim 6 wherein the solvent is tetramethylene sulfone, triethylene glycol dimethyl ether, or a mixture thereof.

8. The process of claim 1 wherein the reaction mixture is heated to a temperature of at least 120° C.

9. The process of claim wherein the reaction mixture initially contains compounds of Formula (III) and, optionally, compounds of Formula (IV),

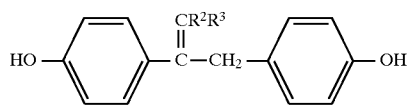

and the molar ratio of the compounds of Formula (I) to compounds of Formulas (III) and (IV) is less than 1:9.

10. A process comprising heating a mixture of: (a) one or more compounds of Formula (I):

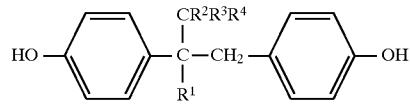

wherein $R^1$ is a hydroxyphenyl group or a group of Formula (II):

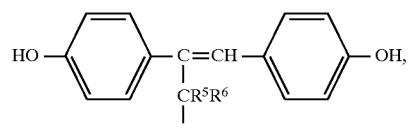

and $R^2$, $R^3$, $R^4$, $R^5$ and $R^6$ are independently in each occurrence H or a $C_{1-10}$ alkyl group; and, (b) at least 0.01 percent by weight, based on the weight of component (a), of a base, to a temperature in the range of from 100° C. to 400° C. under reaction conditions sufficient to convert at least a portion of the compounds of Formula (I) to compounds of Formula (III):

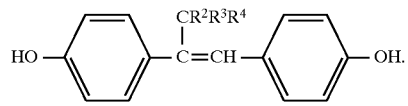

11. The process of claim 10 wherein the base is a sodium alkoxide, sodium hydroxide, sodium phenate, potassium hydroxide, potassium carbonate, potassium phenate, sodium carbonate, or a mixture thereof.

12. The process of claim 11 wherein the base is sodium hydroxide, potassium hydroxide, or a mixture thereof.

13. The process of claim 10 wherein the amount of base is less than 10 percent by weight, based on the weight of component (a).

14. The process of claim 10 wherein the reaction mixture contains a solution of the compounds of Formula (I) and the solvent is selected from the group consisting of aromatic hydrocarbons, aliphatic hydrocarbons, alkyl ethers of polyalkylene glycol, sulfones, sulfoxides, ketones, phenoxy ethers, phenols, amides, or mixtures thereof.

15. The process of claim 14 wherein the solvent is tetramethylene sulfone, triethylene glycol dimethyl ether, or a mixture thereof.

16. The process of claim 10 wherein $R^1$ is hydroxyphenyl or

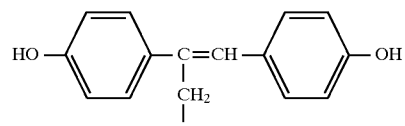

and $R^2$, $R^3$ and $R^4$ are H.

17. The process of claim 10 wherein the reaction mixture is heated to a temperature of at least 150° C.

18. The process of claim 10 wherein the reaction mixture initially contains compounds of Formula (III) and, optionally, compounds of Formula (IV),

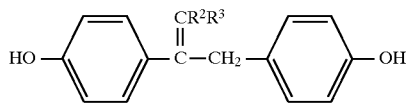

and the molar ratio of the compounds of Formula (I) to compounds of Formulas (III) and (IV) is less than 1:9.

* * * * *